United States Patent [19]
Giesen et al.

[11] Patent Number: 5,723,342
[45] Date of Patent: Mar. 3, 1998

[54] ELECTROCHEMILUMINESENCE ASSAY

[75] Inventors: Ursula Giesen, Weilheim; Nicholas Hoyle, Tutzing; Volker Klemt, Weilheim; Günter Müller, Peissenberg; Ulrich Neumann, Weilheim, all of Germany

[73] Assignee: Boehringer Mannheim GmbH, Mannheim, Germany

[21] Appl. No.: 553,521

[22] PCT Filed: Apr. 27, 1994

[86] PCT No.: PCT/EP94/01329

§ 371 Date: Jul. 11, 1996

§ 102(e) Date: Jul. 11, 1996

[87] PCT Pub. No.: WO94/25854

PCT Pub. Date: Nov. 10, 1994

[30] Foreign Application Priority Data

May 3, 1993 [DE] Germany .................. 43 14 547.7
Sep. 25, 1993 [DE] Germany .................. 43 32 697.8
Jan. 20, 1994 [DE] Germany .................. 44 01 577.1

[51] Int. Cl.$^6$ .................................................. G01N 21/69
[52] U.S. Cl. .......................... 436/172; 422/52; 250/36 K
[58] Field of Search .......................... 436/111, 172, 436/174, 500; 422/52; 250/361 C

[56] References Cited

U.S. PATENT DOCUMENTS

| | | | |
|---|---|---|---|
| 5,061,445 | 10/1991 | Zoski et al. | 422/52 |
| 5,324,457 | 6/1994 | Zhang et al. | 436/172 |
| 5,466,416 | 11/1995 | Ghaed et al. | 422/52 |

FOREIGN PATENT DOCUMENTS 9005296  5/1990  WIPO.

OTHER PUBLICATIONS

Grant, J. Hackh's Chemical Dictionary, 4th ed., McGraw-Hill Book Co., New York, 1972, see definition "temperature, room", p. 664, 1972.

*Primary Examiner*—Jeffrey Snay
*Attorney, Agent, or Firm*—Felfe & Lynch

[57] ABSTRACT

Method for measuring electrochemiluminescent phenomena at low temperatures using alkali chlorides at an increased pH and/or with a reduced initial voltage and reagents and apparatus suitable for this purpose.

20 Claims, 12 Drawing Sheets

ELECTROCHEMILUMINESENCE ASSAY

FIELD OF THE INVENTION

Subject matter of the invention are methods for measuring electrochemiluminescent phenomena, methods for detecting an analyte using said methods, reagent solutions which can be used in said method and an apparatus particularly suitable for carrying out said method.

BACKGROUND AND PRIOR ART

Methods for measuring electrochemiluminescent phenomena have been known for some years. Such methods make use of the ability of special metal complexes to achieve, by means of oxidation, an excited state from which they decay to ground state, emitting electromagnetic radiation. Methods of this kind and suitable metal complexes are described in WO 86/02734, for example.

This technology has continually become more sophisticated. In WO 90/05296, an amine, preferably tripropylamine, which is a strong reducing agent when oxidized, is added to the test composition. The electrochemical reaction occurs in an electrolyte where the electrochemiluminescence (ECL) moiety, i.e. the metal complex able to emit electromagnetic radiation and the amine can be oxidized. The description mentions phosphate buffer at a pH of 6–9, preferably 7–7.5, as a suitable electrolyte in aqueous solution. To increase the electromagnetic radiation, WO 90/05302 proposes to add Triton X-100 or Triton N-401, a detergent, to this test composition. WO 90/05411 describes an improved apparatus for measuring ECL.

Further, it has become possible to use the technology for detecting analytes by coupling electrochemiluminescent labels to analytes, analyte analogs or analyte-specific substances. The electrochemiluminescence was used to determine the quantity of analyte present. The description mentions in particular immunoassays where conventionally used labels are replaced by electrochemiluminescent labels.

Further improvements and applications of this technology are described in WO 87/06706, WO 89/04392, WO 89/10552, WO 89/10551, WO 90/05301, and WO 90/11511. The disclosures of these publications are assumed to be known.

It is, hence, an object of the present invention to improve said known methods, especially with respect to the sensitivity of an analyte detection in combination with electrochemiluminescent procedures.

Fine subject matter of the invention is a method for measuring electrochemiluminescent phenomena in a solution or a solid phase contiguous with a solution, wherein the electrochemiluminescence is measured at a temperature of the solution and/or the solid phase, which is above the freezing point of the solution, but less than 25° C.

Another aspect of the invention is a method for measuring electrochemiluminescent phenomena by generating electrochemiluminescence by applying a voltage to a working electrode. Before the electrochemiluminescence is generated, a potential between +400 and −400 mV, compared to an Ag/AgCl reference electrode, is applied to the working electrode.

Yet another aspect of the invention is a method for measuring electrochemiluminescent phenomena by generating electrochemiluminescence by applying a voltage to a working electrode. Electrochemiluminescence is generated by applying a voltage between the redox potential of the electrochemiluminescent system and +800 mV.

Yet another aspect of the invention is a method for measuring electrochemical phenomena in a solution or a solid phase contiguous with the solution, wherein the solution is a detergent selected from the group consisting of Thesit, C14-E09, Genapol, C8-E09, Plantaren®, and octylglucoside or mixtures thereof.

Yet another aspect of the invention is a method for detecting an analyte by means of said methods, suitable reagents, and an apparatus for carrying out the first mentioned method.

The subject matter of the invention is a teaching based on the above listed prior. The fundamentals of electrochemiluminescent procedures are described in greater detail in the cited prior art documents. Instruments for measuring electrochemiluminescence comprise a measuring unit with a vessel for a reagent solution, at least two electrodes (a working electrode and a counter electrode), which are in contact with the reagent solution during the measurement, and a detector to measure the light generated in the electrochemiluminescent process. Usually, an initial voltage (prepolarization) is first applied to the solution. Subsequently, this voltage is increased via the redox potential of a substance, e.g. an amine, contained in the solution. The so oxidized substance excites a material, e.g. certain ruthenium complexes which are capable of producing chemiluminescence, to emit light. The amount of light received by a detector within a given time interval is a measure for the presence of the amount of electrochemiluminescent material. Provided the electrochemiluminescent material is a label for an analyte, an analyte analog or an analyte-specific substance, e.g. in an immunoassay, the light received is a measure for the presence of the analyte.

Whereas currently known electrochemiluminescent methods operate at temperatures of 28° C. or more, new findings showed that when a ramp voltage with decreasing temperatures is used, the signal strength decreases over the given time unit, but it is surprising to see that the sensitivity increases considerably. This improvement appears to be a consequence of the considerable reduction of non-specific binding between ECL-labeled conjugates to electrodes, for example. At a temperature of 10° C., the amount of non-specific binding can no longer be distinguished from the amount of the background stemming from the reagent solution. It was found that preferred temperatures range between 5° and 20° C. and particularly preferred temperatures between 9° and 11° C. Such temperatures can be achieved either by cooling the reagent solution before it is brought into contact with the measuring unit and/or by cooling it in the measuring unit itself.

Further, it has proven to be advantageous to limit the end voltage applied to the working electrode (compared to Ag/AgCl) to a maximum value between the redox potential of the oxidizable substance and 2.0 V. A voltage between 1.2 and 1.7 V is particularly preferred. An even more particularly preferred voltage is one of 1.6 V. These values apply when platinum electrodes are used.

The sensitivity can further be increased by applying a square-wave voltage to the measuring unit. This means that the initial voltage, is directly increased (within a maximum of 0.4 seconds) to the value of the end voltage. During the excitation time, this voltage is kept essentially constant. After this time, this voltage is directly reduced to a value below the redox potential of the system. Moreover, this measure also improves the dynamic measuring range, i.e. the range in which analyte concentrations of a determined immunoassay can be measured. If lower temperatures are used, the square-wave voltage must be maintained for an excitation time that is extended with respect to higher temperatures. Experience has shown that the intensity measured up to approximately 5 seconds after applying the voltage contributes considerably to the generation of the signal.

The sensitivity or lower detection limit for an analyte can also be improved when the above measures are used either alone or in combination with each other, if the reagent solution which is contained in the measuring unit during the electrochemiluminescent measurement contains an alkali chloride at a concentration of 0.1 mmol/l to 0.5 mol/l. Sodium chloride is a preferred alkali chloride. A particularly preferred concentration for sodium chloride is 0.05 mol/l to 0.45 mol/l; particularly preferred 0.35 mol/l. Moreover, experience has shown that the use of sodium chloride in accordance with the invention reduces the measuring time. Also, the current flow in the cell is increased.

Surprisingly, the signal could also be increased by applying to the working electrode an initial voltage between +400 and −400 mV compared to an Ag/AgCl electrode prior to starting electrochemiluminescence. A particularly preferred value ranges between +50 mV and −50 mV, more particularly 0 mV. These values apply when platinum electrodes are used. The potentials for other electrode materials can be easily calculated.

Further, the signal can also be increased by adjusting the pH to a value between 6.8 and 9.0, preferably between 7.0 and 8.0, particularly preferred between 7.25 and 7.5. This can be done conventionally by using a pH buffer suitable for this range.

Experience has shown that the commonly used detergent Triton X-100, known from WO 90/05302, which is usually employed in combination with the detergent Tween 20, does not produce optimal results. Triton X-100 is difficult to degrade and, hence, is not beneficial to the environment. A180, experience has surprisingly shown that certain detergents other than Triton X-100 improve the ECL method. These special detergents are used to increase the signal yield, to improve the signal/noise ratio thus achieving higher a sensitivity of the detection and to lower the lower detection threshold, and, finally, to achieve a better precision.

Suitable detergents are those from the group consisting of fatty acid alcohol ethoxylates, including, for example, Polidocanol (dodecylpoly-(ethylene glycol ether)$_n$), C14-E09 (poly(ethylene glycol ether)$_n$), Genapol (isotridecylpoly (ethylene glycol ether)$_n$), C8-E09 (octyl alcohol poly (ethylene glycol ether)$_n$) as well as Plantaren® (alkylpolyglucoside) and octylglucoside (octyl-beta-D-glucopyranoside) or a mixture thereof. The detergents are used in concentrations ranging between 0.001 and 1.0%. The optimal concentration can be easily determined for each detergent. The most suitable concentrations are those ranging between 0.1 and 0.5%.

Sodium azide at a concentration of 5–10 mM is normally used as a preservative in this test composition. Experience has shown that this environmentally harmful agent can be replaced by bioban or oxaban which are by far more beneficial to the environment than azide. Surprisingly, these stabilizers have another positive effect on the ECL process, namely an increase of the measurement signal. Oxaban and bioban are used in concentrations of 0.01 to 1%, preferably 0.1 to 0.5%.

The aforementioned measures per se already significantly improve the known procedures. Moreover, it is possible to further significantly increase the sensitivity and/or the dynamic measuring range of analyte detection assays by combining these measures.

The detection limit could further be decreased by means of deoxygenation, e.g. by degassing the reagent interference in a vacuum (e.g. <50 mbar, 2–4 h at room temperature).

When the detection sensitivity of analytes, for example, in immunoassays according to the sandwich principle or the competitive method is increased, the method or the apparatus used can be further simplified. It is, for example, possible to use a photodiode as detector, to simplify system calibration, to increase the number of tests done per time unit since the measuring time is reduced with an increased signal, or to reduce the sample volumes.

Another subject matter of the invention is a reagent solution for measuring electrochemical phenomena and especially for detecting analytes, which comprises an electrochemically oxidizable amine, which is a strong reducing agent when oxidized. The solution contains an alkali chloride in a concentration of 0.1 mmol/l to 0.5 mol/l or has a pH between 7.0 and 8.0. Additionally, the solution can contain a detergent selected from the group consisting of fatty acid alcohol ethoxylate, Plantaren and octoglucoside or a mixture thereof.

Preferred preservative agents for the reagent solutions are bioban or oxaban.

An apparatus for carrying out detections by means of electrochemiluminescence is described in great detail in Example 1 of WO 90/05302, for example. Moreover, such an apparatus can comprise means for cooling the measuring unit and/or a liquid vessel to temperatures between 0° and 25° C. The measuring unit is understood to be a cell in which the electrochemiluminescence is measured. The liquid vessel can be a storage container, but also a feeding device; for example, a tube for the reagent solution, contained in the measuring unit during the measurement.

Also a feature of the invention is a method for detecting an analyte using an electrochemiluminescent label, wherein one of the above listed methods for measuring electrochemiluminescent phenomena is employed.

BRIEF DESCRIPTION OF THE FIGURES

FIG. 5b shows the signal amplituder of magnetic particles, which were shown as signal curves in FIG. 5a.

DETAILED DESCRIPTION OF PREFERRED EMBODIMENTS

The following examples are intended to further illustrate the invention:

EXAMPLE 1

Determination of TSH by applying an electrochemiluminescent procedure

Thyroid-stimulating hormone (TSH) was determined in a sandwich immunoassay. The apparatus used was one as described in example 1 of WO 90/05302 which also contained a permanent magnet in its measuring cell (Origen 1.0 by IGEN, Rockville, USA, or Magnalyser®). Further, the instrument also comprised a photomultiplier, a potentiostat, an electrochemical flow-through cell, liquid transfer agents and a 50-tube sample rotor. The following substances were combined for the detection reaction:

| | | |
|---|---|---|
| Incubation buffer (containing 6.06 g/l Tris × HCl, 1 g/l chloracetamide, 0.1 g/l methylisothiazolon, pH 8.0, 50 g/l bovine serum albumin, 10 g/l Ruthenylated-lgG) | | 50 µl |
| Streptavidin-coated magnetic particles (Dynal, 2.8 µm) in the incubation buffer | 600 µg/ml | 40 µl |
| Monoclonal antibody (MAB) to TSH biotinylated with DSS (disuccinidyl suberate) in the incubation buffer | 3.0 µg/ml | 40 µl |
| TAG: (Tris)(2,2'-bipyridyl)ruthenium chloride hexahydrate bound with DSS to the MAB to TSH in the incubation buffer | 1.2 µg/ml | 40 µl |
| Sample liquid or standard | | 50 µl |
| Resuspension (addition of reagent solution (BMG1)) | | 100 µl |

The streptavidin-coated magnetic particles were purchased from Deutsche Dynal GmbH (Dynabeads M-280 Streptavidin).

This mixture was incubated for 16 minutes at room temperature (21° C.) and then transferred to the measuring cell which was brought to room temperature. The mobilized particles were washed with reagent solution BMG1 and measured in BMG1.

BMG1 has the following composition:

| Reagent | pH 7.5 g/l |
|---|---|
| KH$_2$PO$_4$*2H$_2$O | 27.19 |
| H$_3$PO$_4$ | — |
| Polidocanol | 1.0 |
| Oxaban A | 1.0 |
| TPA (tripropylamine) | 14.33 |
| KOH | 3.6 |

For this example, a TSH immunoassay was used to show the effect of the cell temperature on the signal recovery and the standard curve when a ramp voltage is used.

TABLE 1

Effect of the cell temperature on the signal recovery

| | 21° C. | 28° C. | 35° C. | 42° C. |
|---|---|---|---|---|
| SD | 49.00 | 33.00 | 78.20 | 68.90 |
| CV | 2.59 | 1.48 | 3.30 | 3.60 |
| LDL (2s) | 0.07 | 0.05 | 0.14 | 0.13 |
| LDL (3s) | 0.11 | 0.08 | 0.21 | 0.20 |
| b/a | 1.28 | 1.24 | 1.12 | 1.13 |
| e/a | 65.82 | 45.67 | 33.38 | 27.79 |
| Average a | 1893 | 2248 | 2345 | 1894 |
| Average b | 2421 | 2779 | 2619 | 2139 |

TABLE 1-continued

Effect of the cell temperature on the signal recovery

| | 21° C. | 28° C. | 35° C. | 42° C. |
|---|---|---|---|---|
| Average c | 6918 | 6357 | 5253 | 4103 |
| Average d | 35660 | 30532 | 23695 | 17490 |
| Average e | 124595 | 102674 | 78265 | 52625 |

LDL (2s) or LDL (3s): lower detection limit defined by 2 or 3 standard deviations from the mean of the signal of standard a.

SD: standard deviation

CV: coefficient of variation b/a: ratio of measuring signal of standard b/a e/a: ratio of measuring signal of standard e/a (dynamic range)

c: counts (measurement signal)

The standads a–e had TSH concentrations of:

a: 0 µU/ml b: 0.39 µU/ml c: 3.54 µU/ml d: 12.40 µU/ml e: 94.30 µU/ml

Figure 1:
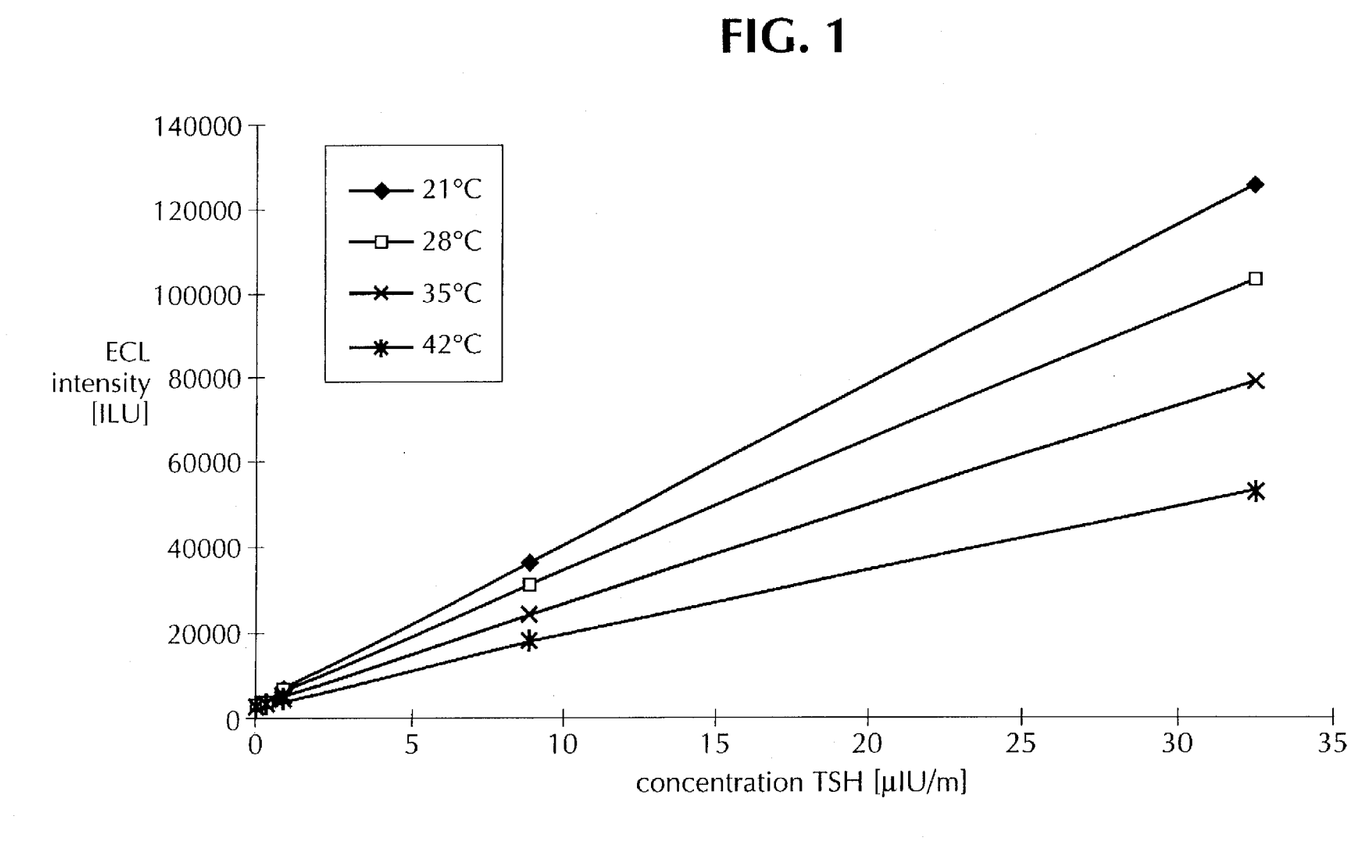
FIG. 1 shows the effect that temperature has on a TSH (thyroid stimulating hormone) assay, when ramp voltage is applied.

The effects of the cell temperature on the standard curve are shown in FIG. 1. The detected chemiluminescence is plotted against the concentrations of 5 standards a–e with different TSH concentrations given in µlU/ml. It is obvious that the light yield increases with lower temperatures when a ramp voltage is applied.

EXAMPLE 2

Figure 2:
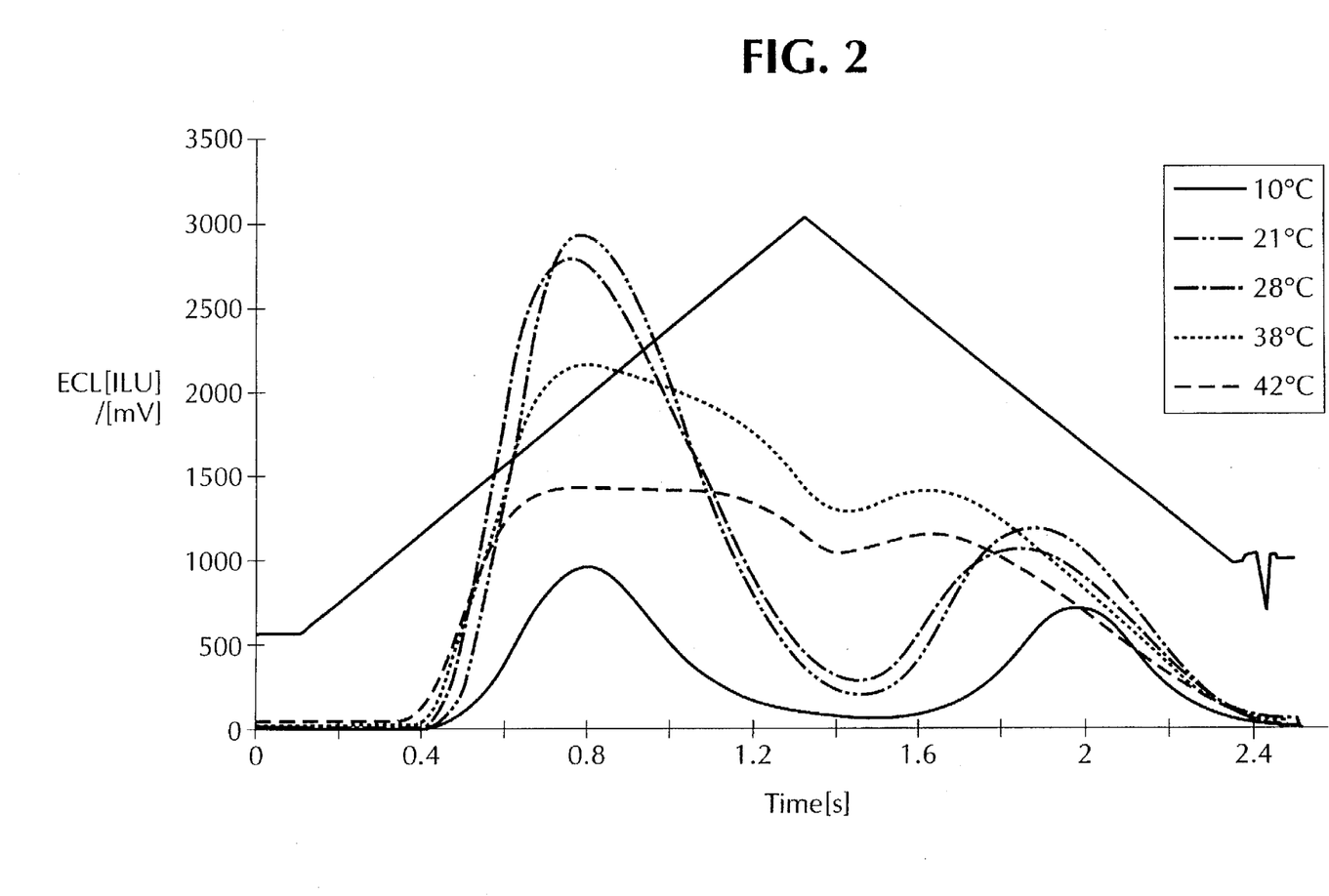
FIG. 2 also shows the effect of temperature in such an assay, in the presence of a buffer.

The effect of the temperature on the determination of TSH according to example 1 in a buffer (BMG1) at a TSH concentration of standard e (see example 2) was measured for different temperatures between 10° and 42° C. The voltage of a so-called ramp voltage was used, where the potential of 565 mV (initial voltage) increased to 3 V over a period of 1 s and subsequently decreased down to 1 V in the same manner. The results are sumarized in FIG. 2. It is obvious that, if a ramp voltage is applied, the intensity of the signal increases from 42° toward 21° C. and then decreases again at 10° C.

EXAMPLE 3

Figure 3:
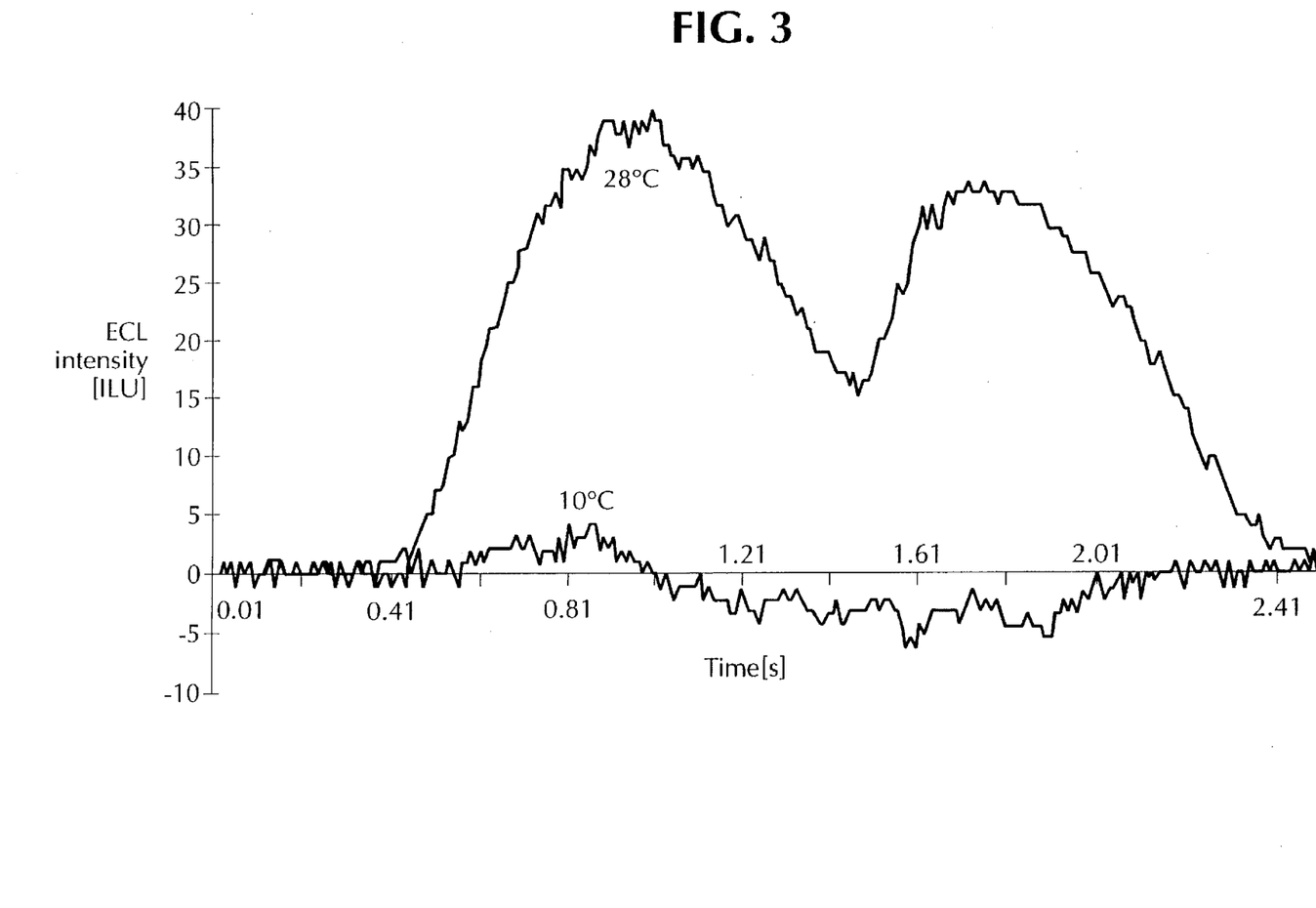
FIG. 3 depicts results secured when a TAG—analyte complex is used without a biotenylated antibody.

The effect on the test-specific background signal, i.e. the signal which is generated solely by the TAG-analyte complex in the absence of the biotinylated antibody, is determined in the buffer BMG1 at 10° and 28° C. The ramp voltage described in example 2 was applied. The results are summarized in FIG. 3. It is obvious that the test-specific, non-specific binding of the TAG-analyte complex decreases with a decreasing temperature.

EXAMPLE 4

Figure 4:
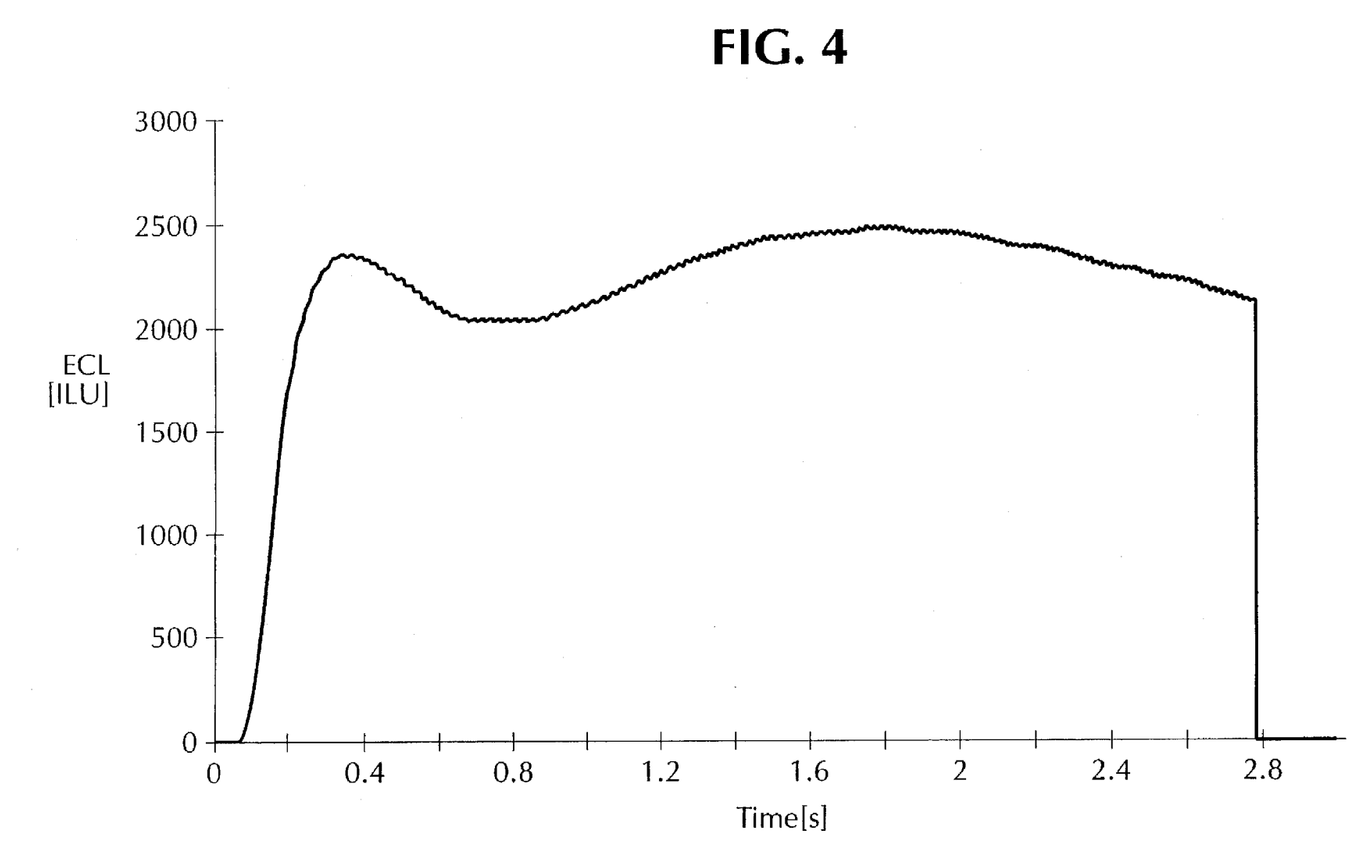
FIG. 4 shows results secured with a square wave voltage, with relatively late time point for measurement.

To determine TSH according to example 1 with the concentration of standard e and buffer BMG1, the time interval of the amount of light detected was measured at 10° C. and with a square-wave voltage beginning at 565 mV. The results are summarized in FIG. 4. It is clear that most of of the radiation intensity must be measured at a relatively late point in time. It must be assumed that so far it has not been possible to measure the intensity which was measured after 0.8 seconds or that investigators have neglected to do it.

When a square-wave voltage was used instead of a ramp voltage, the detection limit for TSH could be reduced from 0.03 μIU/ml down to 0.006 mIU/ml. The dynamic range was improved from 55 to 104. These quotients represent the signal intensity of the standards with the highest concentration (e) to the signal intensity of the standard with the lowest concentration (a).

EXAMPLE 5

Figure 5A:
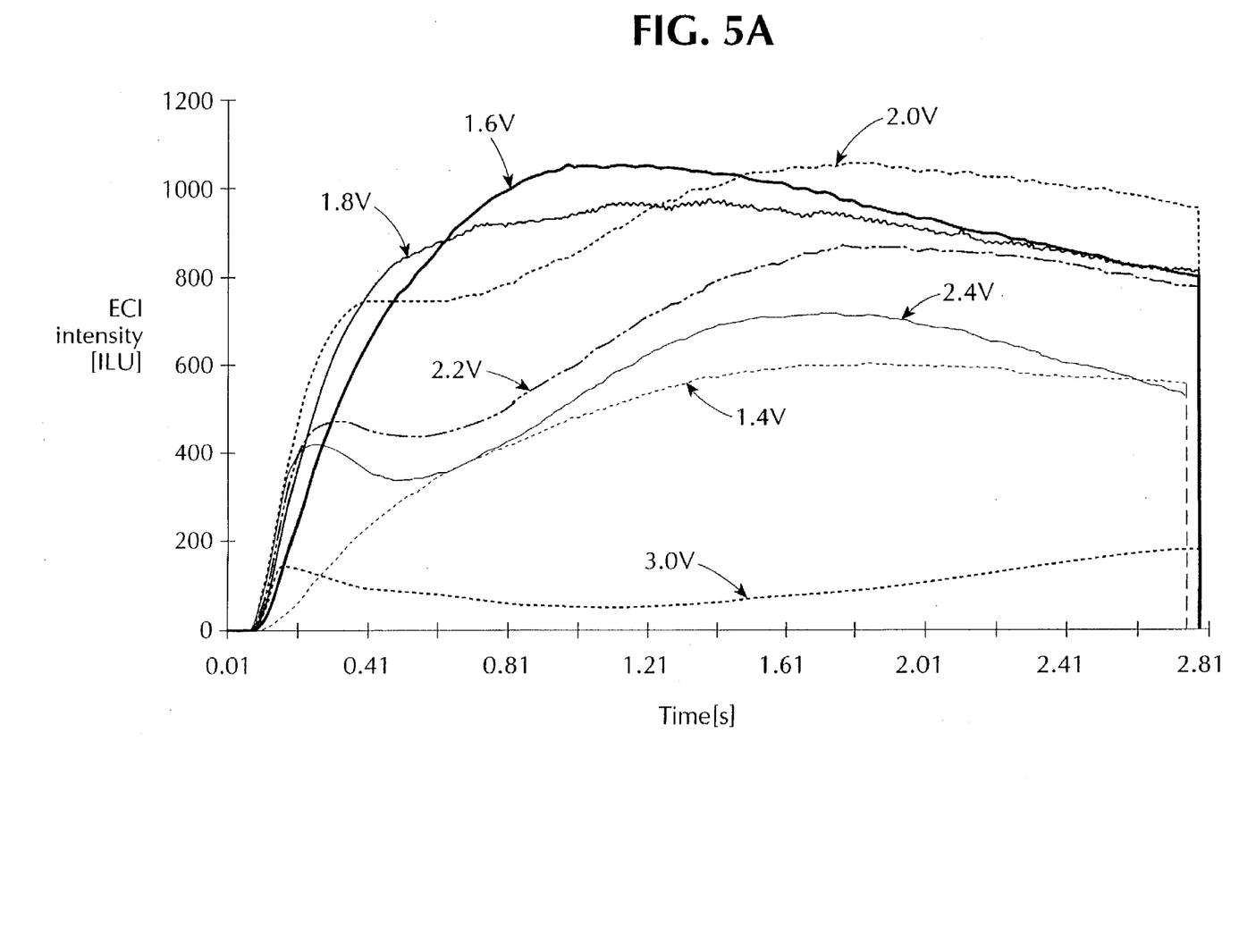
FIG. 5a studies the effect of the size of end voltage.

In a series of experiments, the effect of the size of the end voltage applied to generate electrochemiluminescence on the intensity of the signal was investigated (square-wave voltage). The result is shown in FIG. 5a. Good results were obtained for voltages between 1.6 and 2.0 V. The optimal voltage was 1.6 V.

Figure 5B:
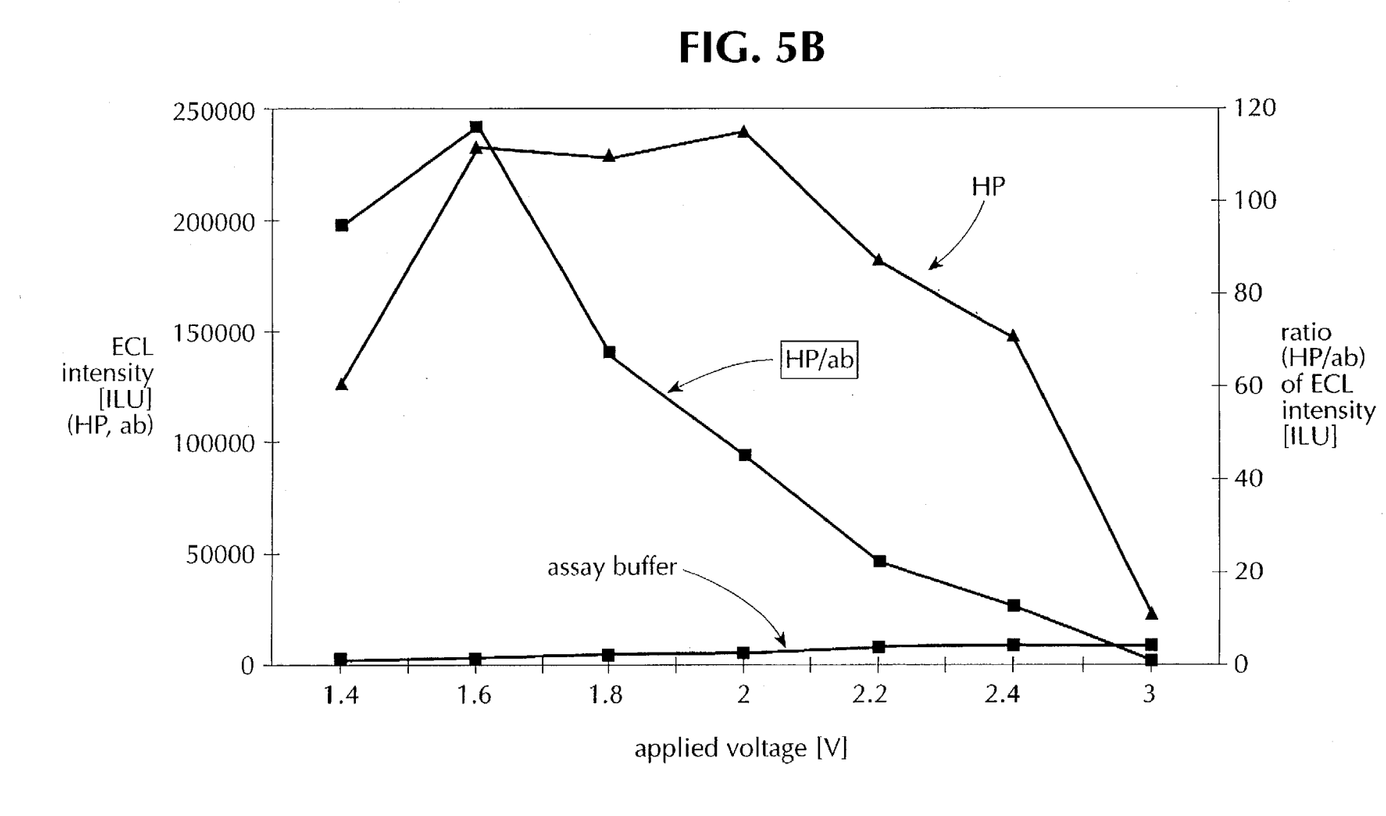

FIG. 5b shows the signal amplitudes of the magnetic particles (HP) which are displayed as signal curves in FIG. 5a. The background signal (ab) and the ratio of the signal amplitudes of the magnetic particles to the background (HP/ab) is also displayed. The essential factor for the selection of the voltage to be used is the signal/noise ratio, i.e. HP/ab. FIG. 5 shows that the maximum value is obtained at 1.6 V.

The measurement was performed in a suspension of magnetic particles which were loaded with an electrochemiluminescent label as follows:

Streptavidin-coated magnetic particles (Dynal, 2.8 μm diameter) together with a conjugate of a biotinylated polyclonal antibody (IgG) to T4, labeled with ruthenium-bis-pyridyl-N-hydroxysuccinimide ester (IGEN, data provided by the manufacturer) was incubated in a buffer (50 mM HEPES pH 7.4; 3% saccharose; 2% bovine serum albumin; 0.01% methylisothiazolon; 0.1% Oxypyrion®) for 1 h at 21° C. in a roller agitator (20 ng conjugate/1 mg particles). The particles were diluted with unlabeled Dynal particles to give a concentration that produces 50,000 units on an ECL measuring instrument (Magnalyser, IGEN). The particles were stored until use in the form of a lyophilisate. Prior to use, the particles were suspended in 4 ml buffer (BMG1) to give a concentration of 600 μg/ml. The particles in portions of 50 μl of suspension were given into Magnalyser test tubes together with 500 μl buffer (BMG1) and measured.

EXAMPLE 6

Effect of the concentration of alkali halogenides on the electrochemiluminescence (ECL) intensity.

In a series of experiments, the TSH test according to example 1 was used to test the effect of the concentration of sodium chloride/potassium chloride on the ECL signal. TSH standard e was used for this experiment. A square-wave voltage of 1.6 V was applied. The initial voltage was 565 mV. The buffer used was BMG1. The temperature was adjusted to 10° C.

It is very obvious that the test results without sodium chloride are very poor, whereas the integrals at concentrations of 0.1 mol/l and 0.25 mol/l are clearly elevated. A similar, but not as obvious, signal difference was obtained for potassium chloride.

Figure 6:
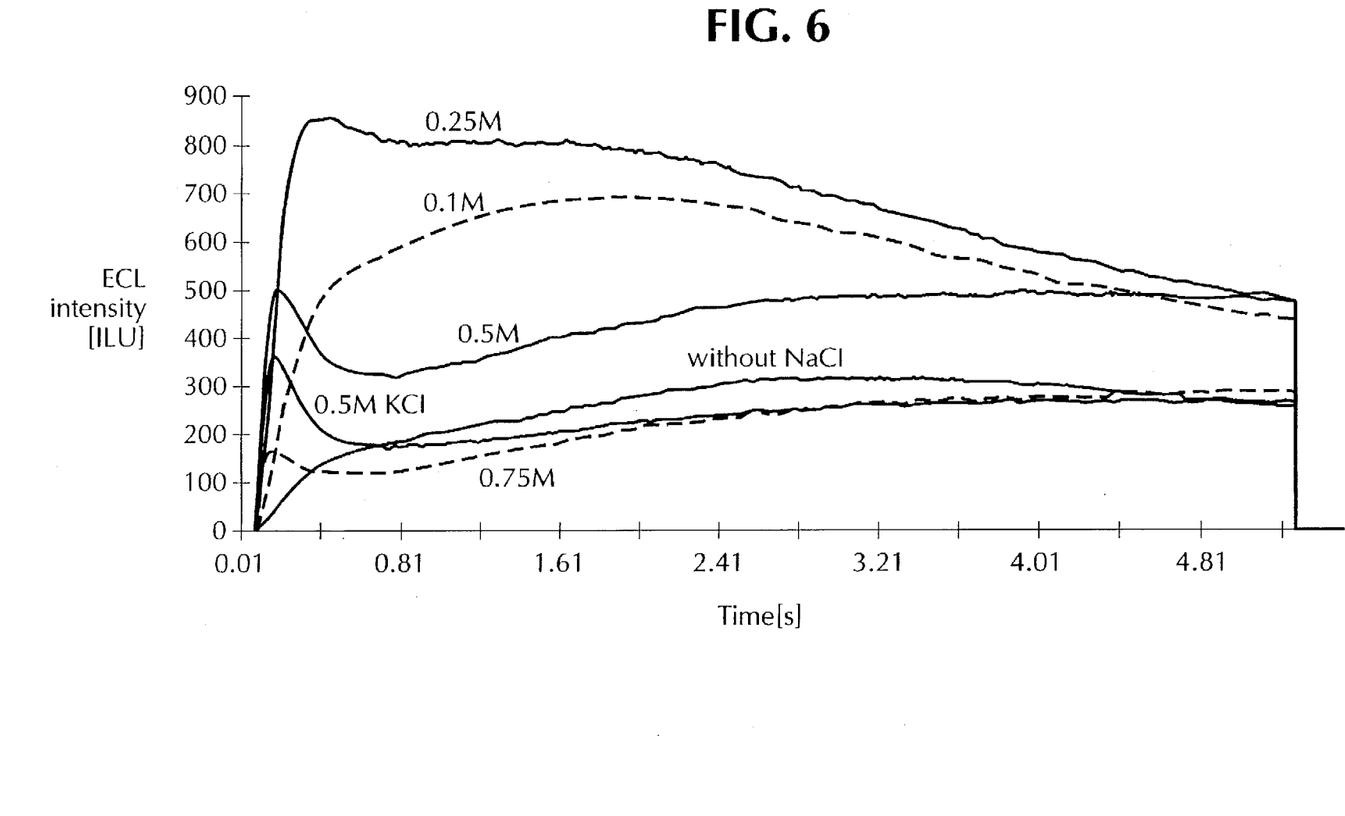
FIG. 6 summarizes results of assays carried out to determine the effect of alkali halides on the system.

The results are summarized in FIG. 6.

EXAMPLE 7

Figure 7:
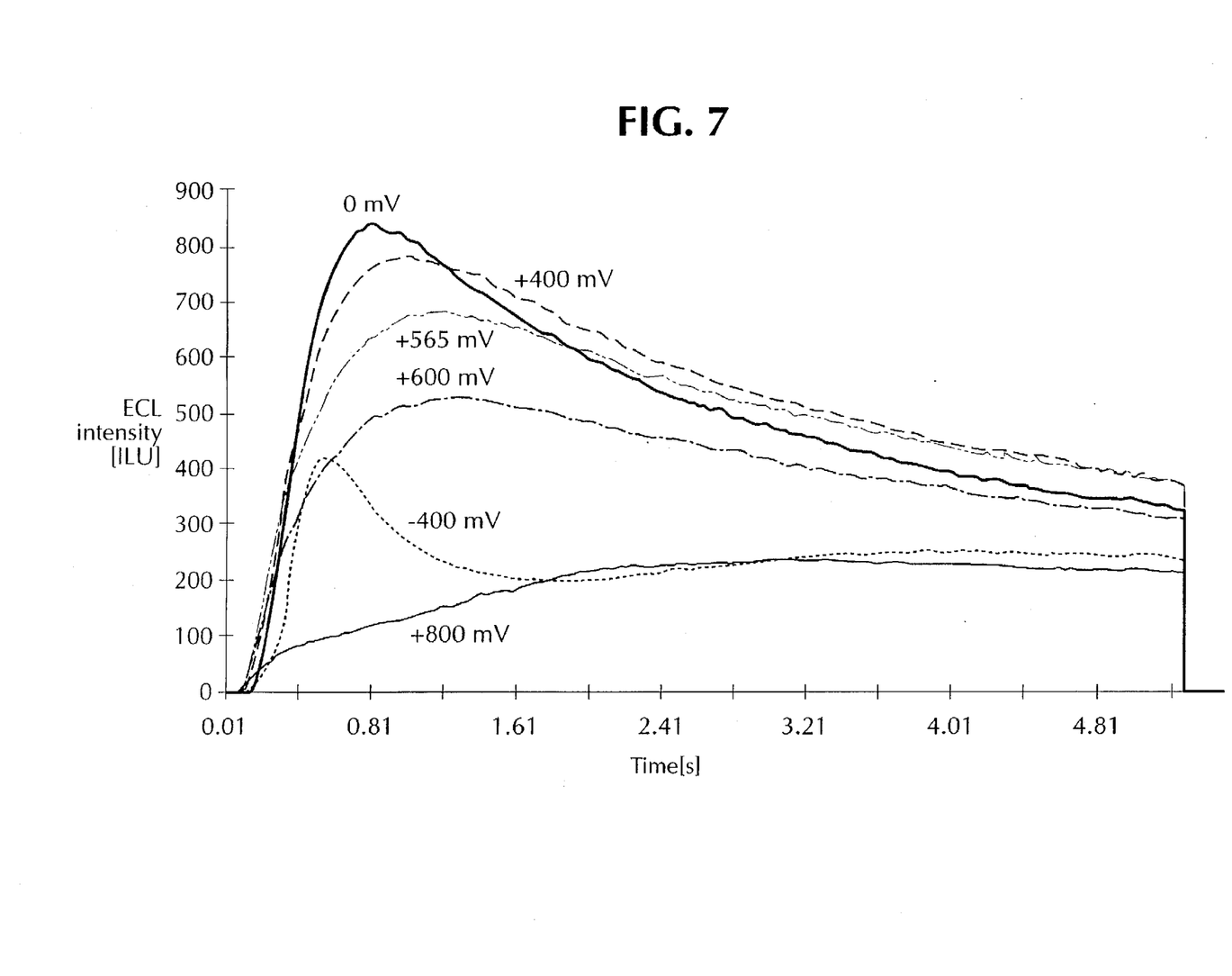
FIG. 7 shows the effect of prepolarization on the assay.

In a series of experiments, the effect of the initial voltage (prepolarization of the working electrode) at 10° C. with BMG1 buffer for TAG-labeled Dynal particles was tested. The ECL voltage used was 1.6 V (square waves). From the drawing of FIG. 7, it is clear that the ECL intensity tends to reach a maximum when the initial voltage approaches 0 mV against Ag/AgCl.

EXAMPLE 8

The effect of the pH in the reagent solution was measured in a TSH test with standard e according to example 1. The following parameters were used in the test:

| Square-wave voltage | 1.6 V (maximum) |
|---|---|
| Initial voltage | 565 mV |
| Temperature | 10° C. |

The example clearly showed that at a pH of 7.5, the intensity of the signal during the measurement interval is significantly increased as opposed to a pH of 6.8 or the buffers described in prior art documents.

Buffer BMG2 has the following composition:

| Reagent | pH 6.8<br>g/l |
|---|---|
| $KH_2PO_4*2H_2O$ | — |
| $H_3PO_4$ | 16.4 |
| Polidocanol | 1.0 |
| Oxaban A | 1.0 |
| TPA (tripropylamine) | 22.93 |
| KOH | 5.7 |

Figure 8:
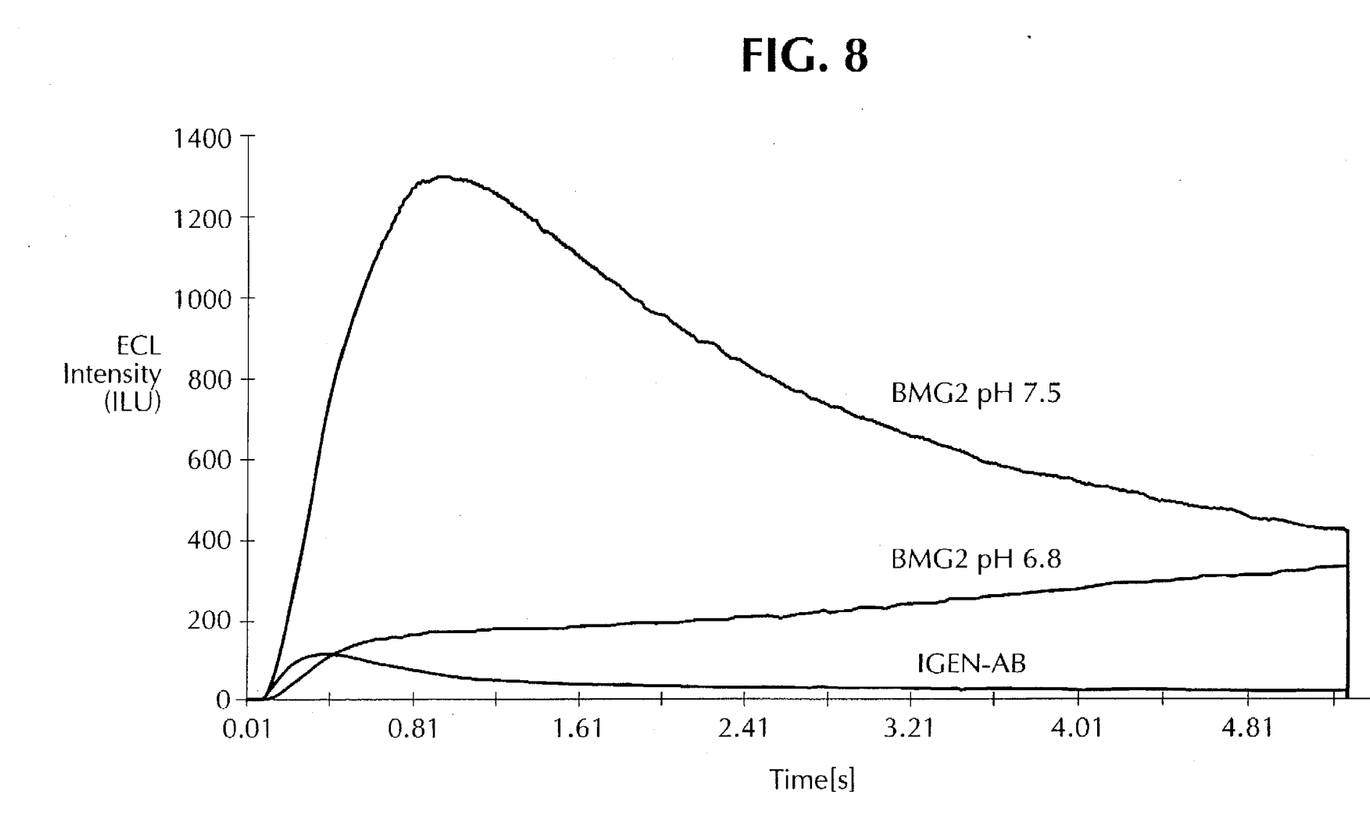
FIG. 8 shows the effect of pH on the assay.

The results are summarized in FIG. 8. The integrated intensity was as follows: at pH 6.8: 112000; and at pH 7.5: 399000.

EXAMPLE 9

The experiments carried out for this example were based on the TSH test according to example 1. They showed that by combining the measures of the invention, the ECL signal can again be considerably increased at a relatively early time. The five curves shown in the diagrams were measured at 10° C. and at an electrochemiluminescence voltage of 1.6 V (square-wave voltage).

Figure 9:
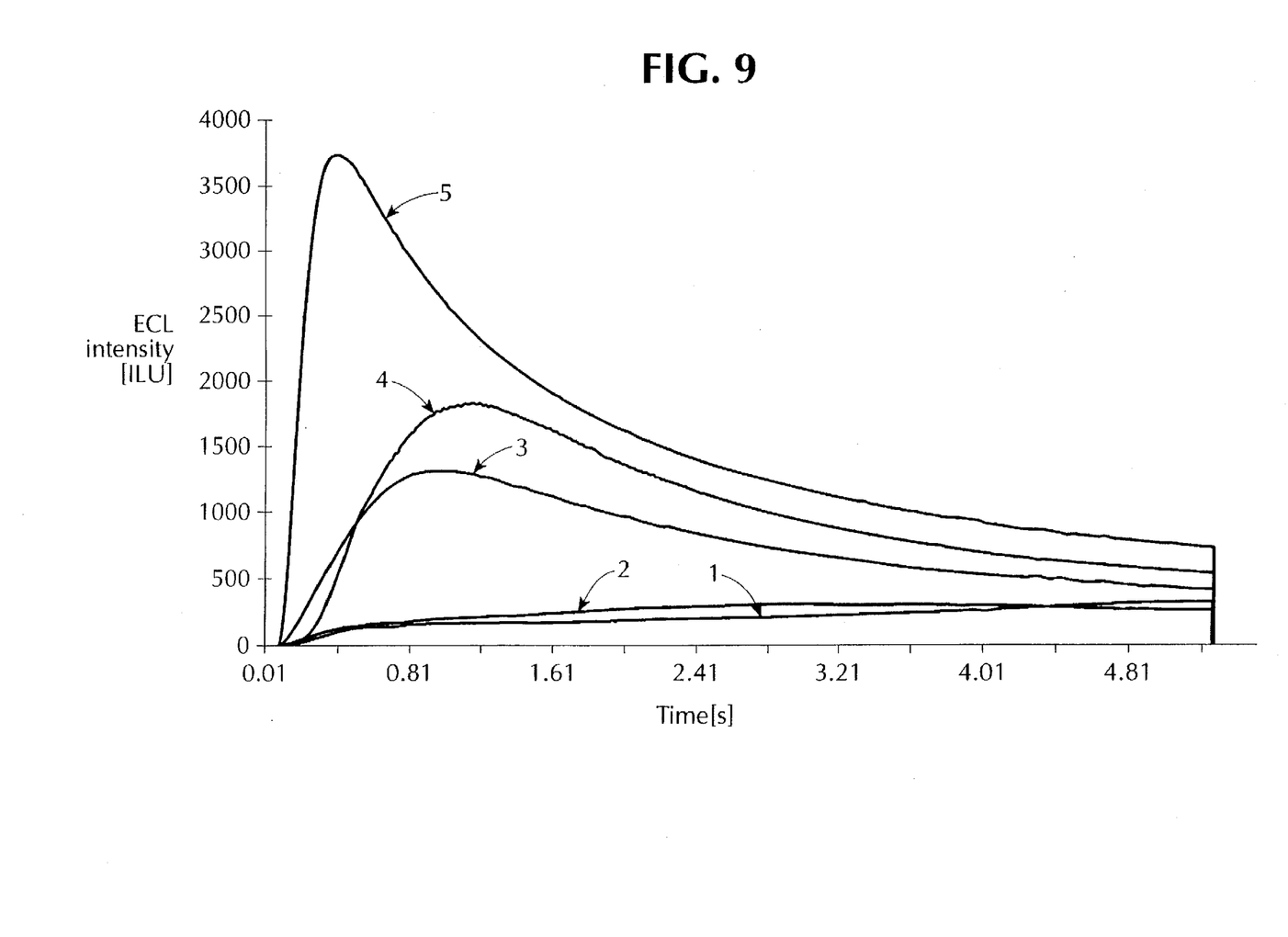
FIG. 9 presents data relating to combining signal results.

Curve 1: BMG2, pH 6.8, initial voltage 565 mV
Curve 2: BMG1, pH 7.5, initial voltage 565 mV
Curve 3: BMG2, pH 7.5, initial voltage 565 mV
Curve 4: BMG2, pH 7.5, initial voltage 0 mV
Curve 5: BMG2, pH 7.5, 0.25 M NaCl, initial voltage 0 mV The results of the experiment are summarized in FIG. 9.

EXAMPLE 10

Figure 10:
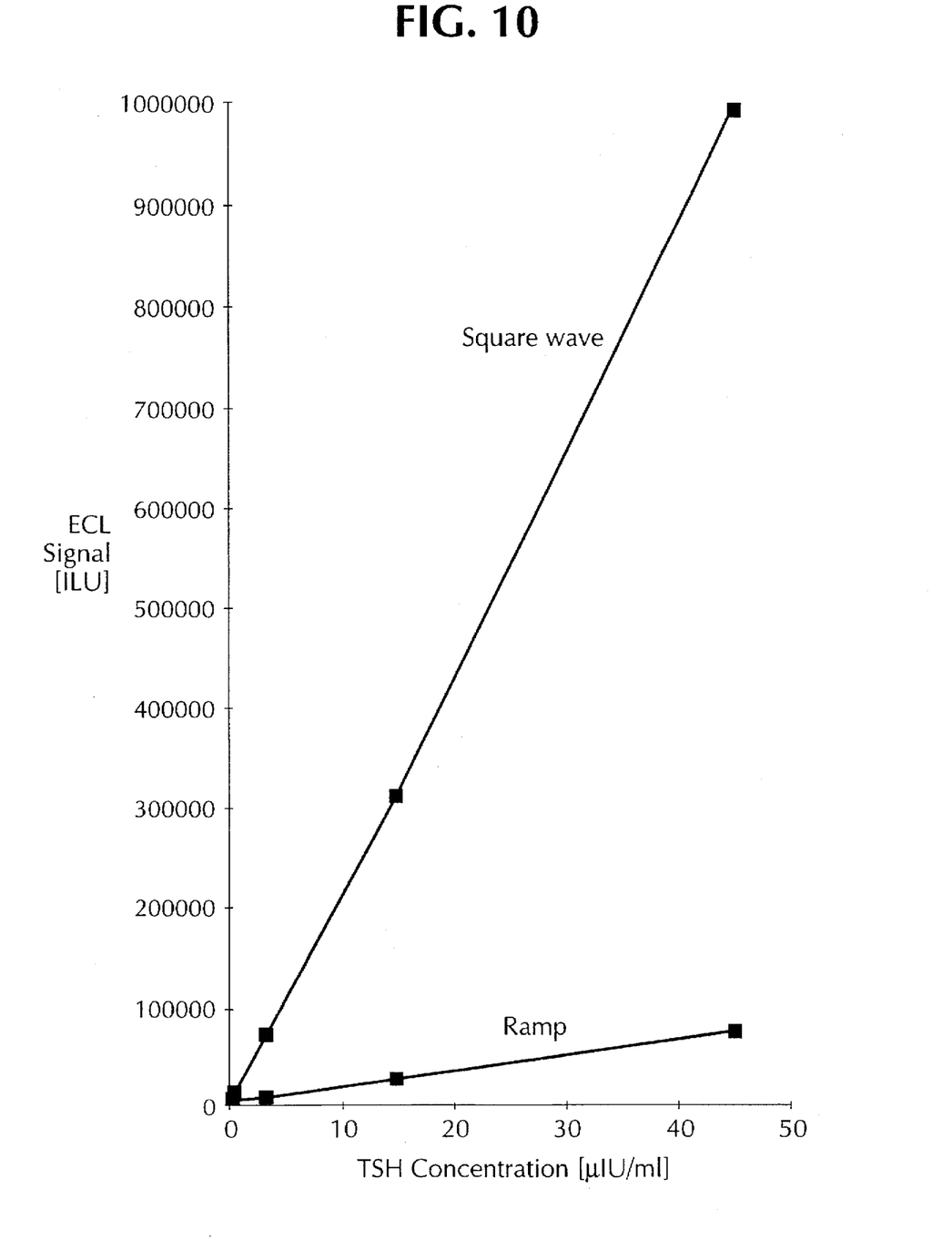
FIG. 10 shows standard curves obtained for TSH determination.

FIG. 10 shows standard curves for a determination of TSH according to example 1 at 10° C. Curve 1 shows the standard curve when a ramp voltage is used (as in FIG. 2), whereas curve 2 shows the standard curve when a square-wave voltage is used combined with an optimized pH, ionic strength and prepolarization conditions. This shows that when low temperatures are used, the intensity of the signal can be increased by applying a square-wave voltage.

The TSH detection limit could be reduced to approximately 0.0028 μIU/ml by combining the measures. The dynamic range was improved to approximately 280 (standard e/standard a).

EXAMPLE 11

Figure 11:
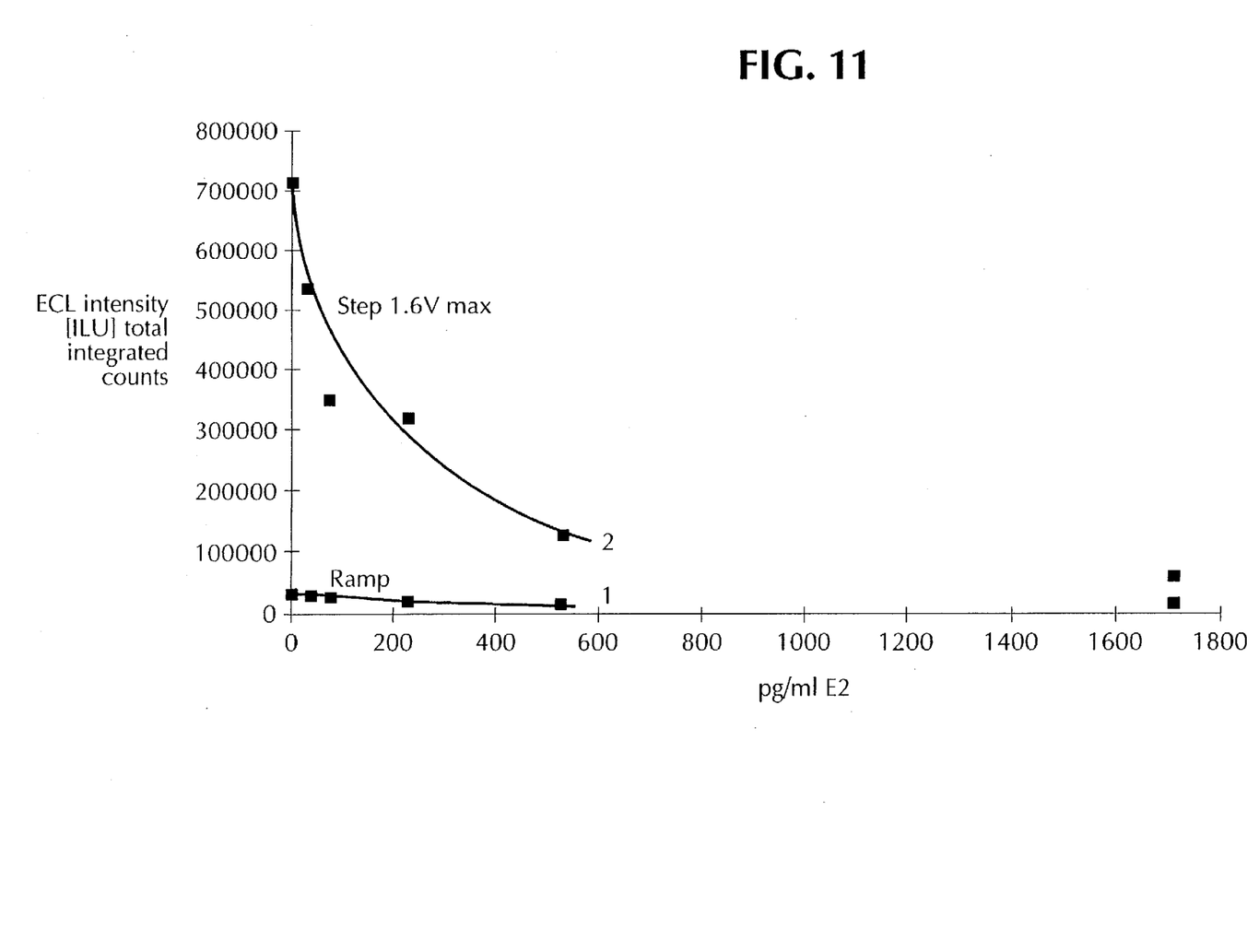
FIG. 11 shows standard curves for estradial determination, comparing prior art assays to the invention.

Additional experiments confirmed that the effect achieved with the invention is also possible with other analytes. FIG.

11 shows the standard curves for a determination of estradiol (E2) under prior art conditions (ramp) and the conditions according to the invention (10° C., square-wave voltage 1.6 V). The sensitivity (lower detection limit) could be increased by a factor of 20 (down to approximately 1.5 pg/ml).

The following components were incubated together for the detection of E2:

1st step:

25 µl buffer BMG 1

50 µl solution of biotinylated (DSS) polyclonal antibody (FAB') against E2

50 µl sample or standard (containing 0.1% thesit, 0.3% bovine serum albumin)

50 mg/ml dihydroxytestosterone

Then the solution was incubated for 15 min.

2nd step:

25 µl buffer BMG 1
50 µl magnetic particle solution from example 1
50 µl TAG solution:
    300 mg/ml FAB fragment to E2, labeled with Ru (bpy)$_3^{2+-NHS-ester}$ by IGEN.

were added.

The solution was also incubated for 15 min. Then 100 µl of it were added to BMG 1, the suspension was transferred into the Magnalyser, the immobilized magnetic particles were washed with 1500 µl BMG 1 and were measured in BMG 1 for the following standards:

| | |
|---|---|
| a | 0 pg/ml |
| b | 72 pg/ml |
| c | 229 pg/ml |
| d | 529 pg/ml |
| e | 1709 pg/ml |
| f | 5032 pg/ml |

EXAMPLE 12

The sole effect of the detergent used in accordance with the invention was determined in a series of experiments. In order to determine the influence of the detergents on the generation of the signal independently of the individual test parameters, i.e. the analytes to be determined, streptavidin-coated magnetic particles to which a biotinylated or ruthenylated antibody was attached, was used (HSAP: "hot streptavidin particle").

The following substances were combined in a reagent tube to carry out the analysis:

HSAP (lyophilized HSAP was dispersed in a Tris/polidocanol buffer (100 mM; 0.1%) pH 9.0 to give a working solution of 600 µg/ml) 50 µl PBS buffer (50 mM KH$_2$PO$_4$ buffer; 100 mM NaCl; 0.1% BSA; pH 7.0) 200 µl Reagent solution (200 mM KH$_2$PO$_4$ buffer; 100 mM TPA (tripropylamine); pH 7.5; for each reagent tested)

This mixture was pipetted into a measuring tube and then transferred into the measuring cell. The HSAP were washed with the buffer (AB) and the signal yield was measured in this buffer.

The antibody used was biotinylated with biotin-DDS (biotinyl-amino-3,6-dioxaoctanoyl-aminocarbonyl-heptanoic acid-N-hydroxysuccinimide ester). (Tris) (2,2'-bipyridil) ruthenium chloride hexahydrate was bound to the antibody by using DSS (disuccinyl suberate).

Dynabeads M-280 Streptavidin by Deutsche Dynal GmbH, Germany were used in the experiments.

The buffer (AB) used in the measurement was composed as follows:

| | |
|---|---|
| KH$_2$PO$_4$*2H$_2$O | 0.2 M |
| KOH | 0.076 M |
| NaCl | 0.05 mM |
| TPA (tripropylamine) | 0.1 M |
| Detergent | concentrations as stated in the table |
| Oxaban/bioban | 0.1/0.3% |
| pH | 7.5 |

The controls used were the commonly known detergents Tween 20 and Triton X-100, each at a concentration of 0.05%. To have a reference, the signal yield obtained with this detergent given in Table 2 was considered to be 100%. To have another measurement value, the non-specific signal yield in the buffer (AB) was determined and used to calculate the ratio of the HSAP/AB signal yield. This ratio between the signal yield with and without HSAP is a good indicator for the sensitivity of the assay. From the results given in Table 1, it can be clearly understood that the detergents of the invention are most suitable. Polidocanol and C8-E09 show the best effect on the HSAP/AB ratio. Detergents other than Tween/Triton X-100 negatively affect the signal yield.

TABLE 2

Detergents tested for the ECL assay buffer
Electrode: BPt3
PMT 700 V

| Detergent in the buffer | HSAP [%] | HSAP/AB [%] |
|---|---|---|
| 0.05% Tween | 100 | 100 |
| 0.05% Triton | | |
| 0.1% Polidocanol | 295.1 | 414.5 |
| 0.4% C14-E09 | 289.2 | 292.8 |
| 0.2% C14-E09 | 346.2 | 308.2 |
| 0.1% C14-E09 | 382 | 343.2 |
| 0.05% C14-E09 | 402.5 | 342.4 |
| 0.4% Genapol | 360.1 | 117.8 |
| 0.2% Genapol | 377.2 | 129.6 |
| 0.1% Genapol | 386.5 | 126 |
| 0.05% Genapol | 361.5 | 140.1 |
| 0.4% C8-E09 | 481.4 | 530.3 |
| 0.2% C8-E09 | 402 | 394.7 |
| 0.1% Plantaren | 219.1 | 200.7 |
| 0.05% Plantaren | 270.6 | 276.3 |
| 0.025% Plantaren | 295.3 | 292.1 |
| 0.2% Octylglucoside | 286.8 | 390.8 |
| Detergents which cannot be used | | |
| 0.2% Tween 20 | 106.9 | 176.3 |
| 0.1% Tween 20 | 114.9 | 184.5 |
| 0.05% Tween 20 | 124.8 | 213.2 |
| 0.2% Triton X-100 | 62.6 | 68.8 |
| 0.1% Triton X-100 | 83 | 154.3 |
| 0.05% Triton X-100 | 115.6 | 195.4 |
| 0.2% C16-E09 | 17.3 | 36.8 |
| 0.05% C16-E09 | 50 | 98 |
| 0.2% Dodecyl maltoside | 17.7 | 50 |
| 0.1% Dodecyl maltoside | 46.9 | 112.5 |
| 0.2% SDS | 4.1 | 5.6 |
| 0.1% SDS | 22.9 | 32.9 |
| 0.2% Ralufon 3-14 | 27.3 | 29 |
| 0.1% Ralufon 3-14 | 27.8 | 31.3 |

Names and abbreviations of the detergents used
C8-E09: Octylalcoholpoly(ethylene glycol ether)$_n$
C14-E09: Poly(ethylene glycol ether)$_n$
C16-E09: Cetylpoly(ethylene glycol ether)$_n$ TABLE 2-continued Detergents tested for the ECL assay buffer
Electrode: BPt3
PMT 700 V

| Detergent in the buffer | HSAP [%] | HSAP/AB [%] |
|---|---|---|

Dodecyl maltoside: Dodecyl-β-D-glucopyranosyl(1→4)α-D-glucopyranoside
Genapol: Isotridecylpoly(ethylene glycol ether)$_n$
Octylglucoside: Octyl-β-D-glucopyranoside
Plantaren: Alkylpolyglucoside (C14-C16)
Ralufon 3-14: n-Tetradecyl-n,n-dimethyl-3-amino-1-propane sulfate
SDS: Sodium lauryl sulfate
Polidocanol: Dodecylpoly(ethylene glycol ether)$_n$
Triton X-100: Octylphenolpoly(ethylene glycol ether)$_n$
Tween: Poly(oxyethylene)n-sorbitane-monolaurate

We claim:

1. In a method for measuring electrochemiluminescence of a component capable of generating electrochemiluminescence by contacting said component with a solution which contains an oxidizable amine, applying an electrical voltage to said component and said solution to induce electrochemiluminescence, and detecting induced electrochemiluminescence, the improvement comprising cooling said solution to below room temperature and measuring said electrochemiluminescence at a temperature greater than the freezing point of said solution but below about 25° C.

2. The method of claim 1, wherein said component is bound to a solid phase.

3. The method of claim 1, wherein said component is in solution.

4. The method of claim 1, comprising measuring electrochemiluminescence at a temperature between about 5° C. and about 20° C.

5. The method of claim 1, wherein said solution further comprises at least one alkali halide.

6. The method of claim 1, wherein said solution further comprises at least one earth alkali halide.

7. The method of claim 1, wherein said solution has a pH of from about 6.8 to about 9.0.

8. The method of claim 1, comprising determining electrochemiluminescence by applying a maximum voltage of 2.0 V.

9. The method of claim 1, comprising determining electrochemiluminescence by applying a square-wave voltage.

10. The method of claim 1, further comprising adding a fatty acid alcohol ethoxylate to said solution.

11. The method of claim 10, wherein said fatty acid alcohol ethoxylate is dodecylpoly—(ethylene glycol ether)n, poly (ethylene glycol ether)n, isotridecylpoly (ethylene glycol ether)n, or octyl alcohol poly(ethylene glycol ether)n.

12. In a method for determining an analyte in a sample by contacting said sample with an electrochemiluminescently labelled substance selected from the group consisting of labelled analyte analog, and a labelled analyte specific substance and determining electrochemiluminescence as a determination of said analyte in said sample, the improvement comprising cooling said solution to below room temperature and measuring said electrochemiluminescence at a temperature greater than the freezing point of said solution but below about 25° C.

13. The method of claim 12, comprising measuring electrochemiluminescence at a temperature between about 5° C. and about 20° C.

14. The method of claim 12, wherein said solution has a pH of from about 6.8 to about 9.0.

15. The method of claim 12, comprising determining electrochemiluminescence by applying a maximum voltage of 2.0 volts.

16. The method of claim 12, comprising determining electrochemiluminescence by applying a square wave voltage.

17. The method of claim 12, further comprising adding a fatty acid alcohol ethoxylate to said solution.

18. The method of claim 17, wherein said fatty acid alcohol ethoxylate is dodecylpolyethylene glycol ether)n, isotridecylpoly (ethylene glycol ether)n, or octyl alcohol poly (ethylene glycol ether)n.

19. The method of claim 17, further comprising adding at least one alkali halide to said solution.

20. The method of claim 19, further comprising adding at least one earth alkali earth halide to said solution.

* * * * *

UNITED STATES PATENT AND TRADEMARK OFFICE
CERTIFICATE OF CORRECTION

PATENT NO. : 5,723,342  
DATED : March 3, 1998  
INVENTOR(S) : Giesen et al.

Page 1 of 1

It is certified that error appears in the above-identified patent and that said Letters Patent is hereby corrected as shown below:

Title page,  
Item [54]"Electrochemiluminescence Assay" to read as -- Electrochemiluminescent Process --.

Column 1,  
Line 48-49, insert the heading "SUMMARY OF THE INVENTION" between line 48 and 49.  
Line 49, before "subject", "Fine" should read -- The --.

Column 3,  
Line 38, change " A180," to read -- Also --.

Column 6,  
Line 27, change "94.30" to read as -- 44.30 --.

Signed and Sealed this

Fifteenth Day of January, 2002

Attest:

Attesting Officer

JAMES E. ROGAN  
Director of the United States Patent and Trademark Office